United States Patent [19]

Feit

[11] Patent Number: 4,623,348

[45] Date of Patent: Nov. 18, 1986

[54] PERCUTANEOUS SINUS TRACT MAINTENANCE PROSTHESIS

[76] Inventor: Fredric Feit, 1151 Brighton Beach Ave., Brooklyn, N.Y. 11235

[21] Appl. No.: 639,929

[22] Filed: Aug. 13, 1984

[51] Int. Cl.[4] .......................... A61F 2/02; A61B 19/00
[52] U.S. Cl. ...................................... 623/11; 623/12; 623/66; 128/1 R; 604/264; 604/268
[58] Field of Search .................. 3/1 A, 1; 128/1 R; 604/284, 280, 264, 268, 272, 275, 332, 338; 623/12, 66, 11

[56] References Cited

U.S. PATENT DOCUMENTS

| | | | |
|---|---|---|---|
| 1,147,408 | 7/1915 | Kells | 604/272 X |
| 2,765,790 | 10/1956 | Dickson | 604/338 |
| 3,421,509 | 1/1969 | Fiore | 604/280 X |
| 4,321,914 | 3/1982 | Begovac et al. | 128/1 R |

*Primary Examiner*—Richard J. Apley
*Assistant Examiner*—Alan W. Cannon
*Attorney, Agent, or Firm*—Henry R. Lerner

[57] ABSTRACT

A device and method for the continued maintenance of percutaneous sinus tracts between medical catheterization procedures. The device comprises an outer tubular and inner cylindrical members designed to be used with a flexible catheter introduced surgically or with the aid of a trocar device. The method comprises the steps of initially introducing the catheter; sleeving the outer tubular member over the catheter until its outer portion rests against the newly formed sinus tract; completing the desired catheterization procedure; removing the catheter while leaving the outer tubular member in place along the sinus tract; sealing the sinus tract by introduction of the inner cylindrical member into the outer tubular member. As a result the integrity of the sinus tract is maintained for subsequent catheterizations. When a new catheterization is desired the inner cylindrical member is removed; the new catheter is introduced and the members of the invention replaced if subsequent catheterizations are desired. The method can be practiced by skilled technicians or trained family members overcoming the previous need for the attendance of a physician.

11 Claims, 13 Drawing Figures

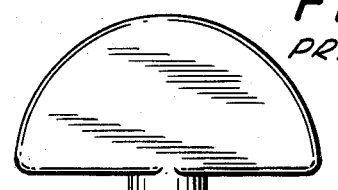
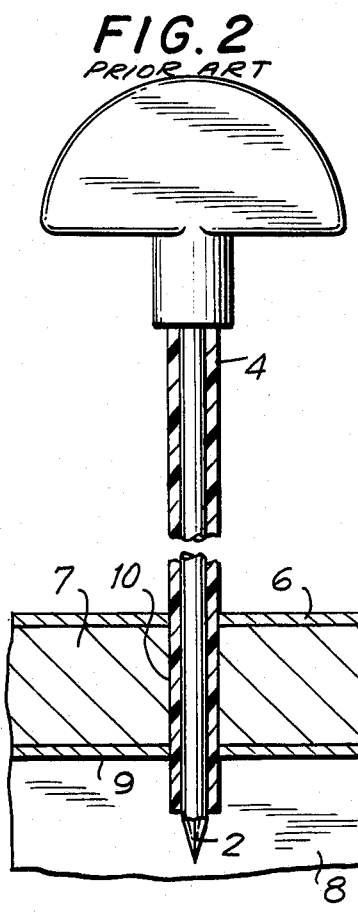
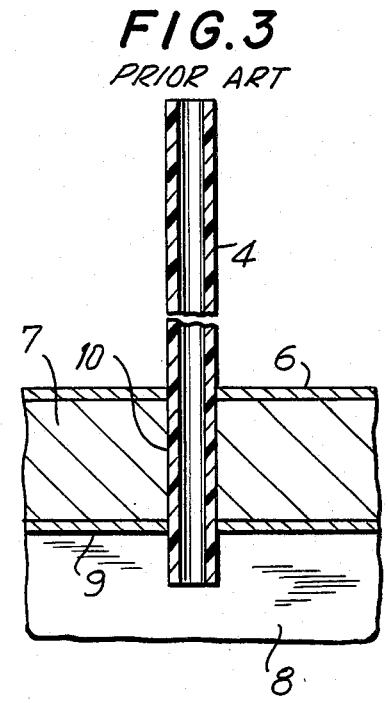
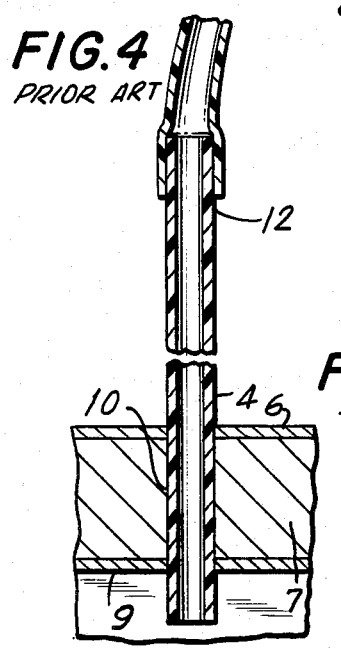
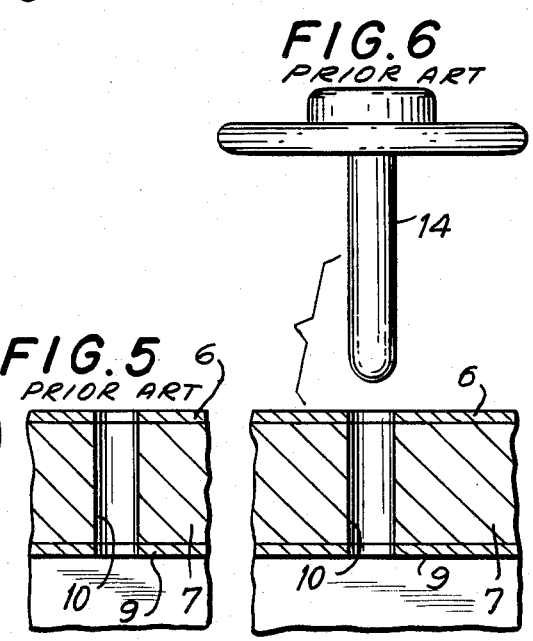
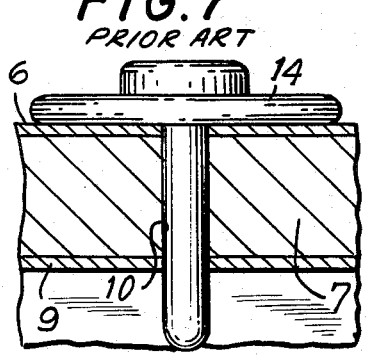

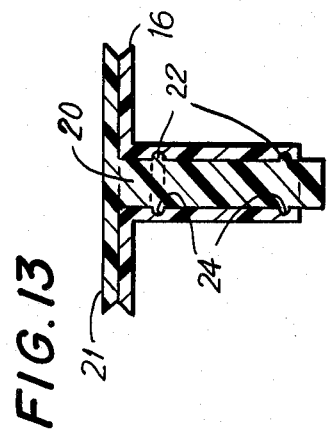
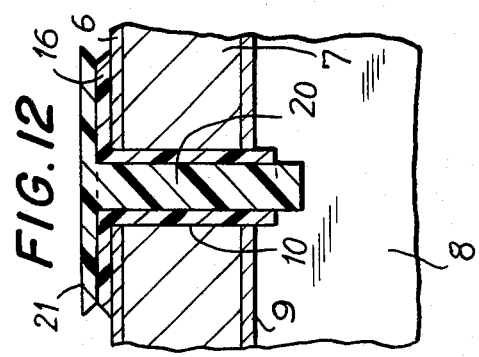
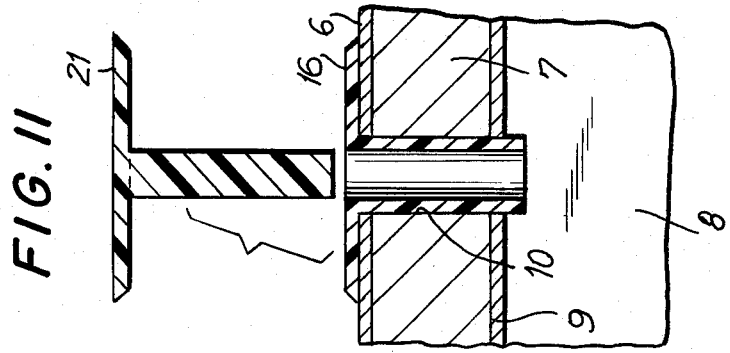
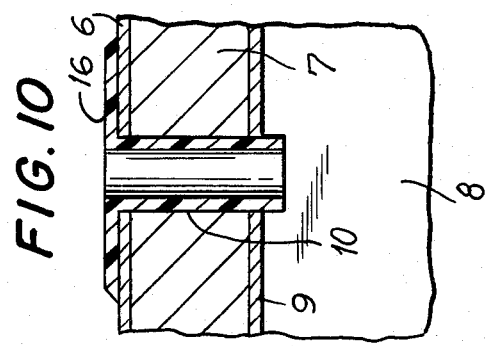
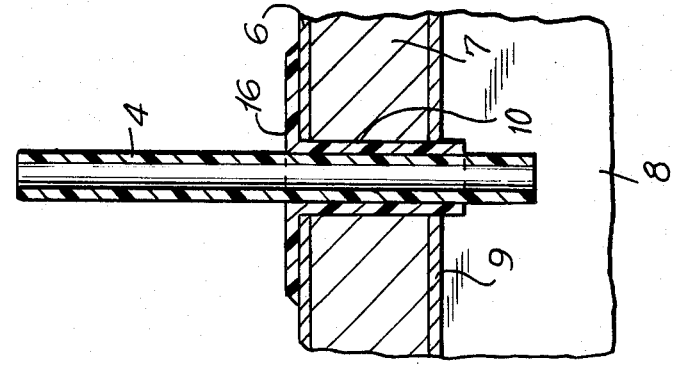
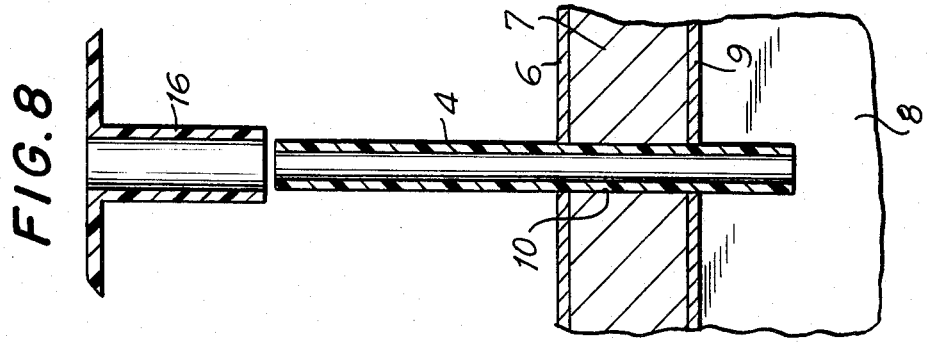

PERCUTANEOUS SINUS TRACT MAINTENANCE PROSTHESIS

BACKGROUND OF THE INVENTION

This invention relates to a device for the maintenance of a percutaneous sinus tract made for the purposes of introduction or removal of fluids or material by catheterization.

Chronic intermittent sinus tract access is required for a variety of medical procedures such as, for example, catheterization for the purposes of chronic peritoneal dialysis.

The standard procedure for chronic peritoneal dialysis is effectuated by implantation of a silastic catheter surgically, under general or regional anesthesia, or with a trocar or a stylet device.

One trocar device for such purposes is more fully described in U.S. Pat. Nos. 3,064,653 and 3,149,186. Such device is commonly known as a "Trocath Peritoneal Dialysis Catheter" (trocar), and is comprised of a catheter, stylet (trocar) and device for attachment to dialysis equipment.

The trocath is comprised of a metal stylet with handle (trocar) and a catheter sleeved around the stylet. It is also usually provided with a connecting device for attachment to the catheter after insertion.

The trocath catheter and stylet are introduced through an enlarged puncture site in the epidermis and then carefully pushed through the peritoneal cavity resulting in the formation of a sinus tract enclosing the catheter and stylet. The stylet is then removed and the catheter is introduced further into the peritoneal cavity to rest in the left or right pelvic gutter. Thereafter a dialysis apparatus is connected to the connecting means attached to the catheter. Dialysis treatment is then effectuated.

After any catheter treatment has been completed, it is usually desirable to remove the catheter between procedures such as in the case of chronic peritoneal dialysis. However, this sometimes results in the undesirable loss of the sinus tract which has been formed by surgery or a trocar stylet thereby making it necessary to form a new sinus tract with the aid of a physician before the next treatment. Also, it is most desirable to avoid repetition of the sinus tract formation procedure for subsequent treatments.

Previously maintaining the integrity of the sinus tract for intermittent dialysis procedures has been attempted by the use of a device described in U.S. Pat. No. 3,505,988 commonly known as "Deane's Peritoneal Prosthesis". Deane's prosthesis is comprised of a pliable plastic rod with a terminal disc. The Deane's prosthesis is introduced into the empty sinus tract subsequent to catheter removal and remains in place with the plastic rod in the sinus tract and the terminal disc resting on the epidermis. It is then normally secured with adhesive tape. The Deane's prosthesis is then left in place until just prior to subsequent catheter reintroduction.

However, when a solid one piece peritoneal prosthesis, such as the Deane's prosthesis, is utilized, it has been found that prior to the insertion of a peritoneal catheter after removal of the prosthesis, the sinus tract to the peritoneum is lost approximately 15% of the time and reintroduction of a new peritoneal trocar or further surgery is required to establish a new sinus tract to the peritoneum, again requiring the attendance of a skilled physician and carrying its associated morbidity. Additionally reintroduction of a catheter when only using Deane's prosthesis to maintain sinus tract integrity requires the use of a reluctantly stiff catheter precluding the use of more flexible catheters.

An object of this invention is to provide a prosthesis which will easily maintain a sinus tract between catheterizations.

Another object of this invention is to provide a prosthesis which, while maintaining sinus tract integrity, also forms a guide for reintroduction of a catheter.

Another object of this invention is to provide a prosthesis which provides an easy means of "sealing" the sinus tract between catheterizations, while maintaining the integrity of the sinus tract, to reduce the risk of infection or the undesirable introduction or loss of material through the sinus tract.

Another object of this invention is to provide a prosthesis which maintains the integrity of the sinus tract and allows for the introduction of a catheter through the sinus tract to the peritoneum or other location without the necessity of the attendance of a skilled physician.

Another object of this invention is to provide a prosthesis for sinus tract maintenance which is easy to use and will be subject to widespread use.

Other objects, features and advantages of the invention will become more apparent from the following description.

SUMMARY OF THE INVENTION

The present invention may be utilized in any procedure which requires catheterization through a formed tract in any somatic wall, membrane or tissue structure, but will be described as applied to catheterization for the purposes of peritoneal dialysis, such being a particularly useful application of the invention.

In accordance with the principles of this invention, the above objects are accomplished by introducing around the in place catheter in a surrounding relationship, an outer hollow tubular member with flange which, when inserted into the sinus tract, with the flange resting on the epidermis, results in the sinus tract resting against the outer wall of said outer tubular member in an abutting relationship thereby maintaining the integrity of the sinus tract. After completion of the medical procedure requiring catheterization, the catheter is removed from the outer tubular member along the sinus tract and the second part of the prosthesis, an inner solid cylindrical member is securely inserted into the outer tubular member to close or seal the sinus tract opening. When a subsequent catheterization is required, the solid inner cylindrical member is removed and a new catheter is easily inserted within the outer tubular member along the original sinus tract thereby utilizing the original sinus tract. While the new catheter is in place, the outer tubular member of the prosthesis may be replaced and the above procedure repeated with a new sterile inner cylindrical member thereby maintaining the originally formed sinus tract for yet another medical procedure requiring the use of a sinus tract for a subsequent catherization.

This new peritoneal prosthesis may allow patients that are being maintained on peritoneal dialysis in a hospital setting, to receive peritoneal dialysis in a non-hospital setting, including at home with the aid of properly trained nursing or similar personnel or an adequately trained family member. This is made possible because without use of the present invention a physician must be available to introduce a peritoneal trocar if the sinus tract to the peritoneum is lost when the present peritoneal prosthesis is withdrawn. However a properly trained nursing or similar personnel or family member may readily be taught to reintroduce a peritoneal dialysis catheter by means of the present invention.

Finally for the first time a peritoneal dialysis prosthesis can be used for the chronic maintenance of a sinus tract within the peritoneum, with neglible risk of losing this sinus tract.

BRIEF DESCRIPTION OF THE DRAWINGS

FIG. 1 is a schematic of a Trocath Peritoneal Dialysis Catheter (trocath) about to be introduced into the epidermis in accordance with prior art procedures.

FIG. 2 shows the trocath in FIG. 1 after introduction through the epidermis and the peritoneum into the peritoneal cavity.

FIG. 3 shows the catheter of FIG. 2 in place within a sinus tract after removal of the trocar stylet.

FIG. 4 shows the catheter in FIG. 3 in place and attached to a connecting means to a dialysis device.

FIG. 5 shows the sinus tract after removal.

FIG. 6 shows the sinus tract after catheter removal with a Deane's prosthesis about to be introduced therein in accordance with prior art procedures.

FIG. 7 shows the Deane's prosthesis shown in FIG. 6 in place within the sinus tract in accordance with prior art procedures.

FIG. 8 is a schematic showing the hollow outer tubular member of the prosthesis in accordance with the invention about to be inserted around the in place catheter and along the sinus tract.

FIG. 9 shows the outer tubular member of the prosthesis in place around the catheter and along the sinus tract with the flange resting on the epidermis.

FIG. 10 shows the outer tubular member of the prosthesis in place along the sinus tract as in FIG. 9 after catheter removal.

FIG. 11 shows the outer tubular member of the prosthesis in place as in FIG. 10 and with the inner cylindrical member of the prosthesis about to be introduced into the outer tubular member.

FIG. 12 shows the outer tubular member of the prosthesis in place along the sinus tract and the inner cylindrical member in place within the outer tubular member of the prosthesis.

FIG. 13 shows the outer tubular member of the prosthesis in place and the inner cylindrical member in place within the outer tubular member with a ridge and groove securing means.

DETAILED DESCRIPTION

FIGS. 1 through 7 illustrate the prior art methods of sinus tract formation and maintenance of sinus tract integrity. FIGS. 8 through 12 illustrate the prosthesis in accordance with the principles of the invention showing its application in catheterization for peritoneal dialysis. However, the principles of the invention are not limited to use of the invention for peritoneal dialysis as the invention may be used in connection with any medical procedure requiring tract formation and maintenance for catheterization purposes in any somatic wall, membrane or tissue structure.

Referring to the drawings, particularly FIGS. 1 through 7, a trocar stylet 2 within a catheter 4 is introduced into the epidermis 6 at an enlarged puncture site therein. The sharpened point of the stylet 2 is used to part the tissue to form the sinus tract 10 which is further enlarged by the introduction of the catheter 4. The stylet 2 within the catheter 4 is then gently pushed through the epidermis 6 into the subdermal tissue 7 resulting in the formation of a sinus tract 10 around the catheter 4 in an abutting relationship to the catheter 4, containing the stylet 2. The stylet 2 and catheter 4 are then further gently pushed through the subdermal tissue 7 until the peritoneum or peritoneal wall 9 is reached. The stylet 2 with catheter 4 surrounding it are then gently pushed through the peritoneum or peritoneal wall 9 until the stylet 2 and catheter 4 are in place in the peritoneal cavity 8 along a formed sinus tract 10 as shown in FIG. 2. The stylet 2 is then removed and the catheter 4 is then gently pushed further into the peritoneal cavity 8 along the formed sinus tract 10 until the catheter 4 rests in either the left or right pelvic gutter (not shown) as shown in FIG. 3. Thereafter, a connecting means 12 is attached to the catheter 4, said connecting means 12 being attached to the dialysis apparatus (not shown) as shown in FIG. 4. After dialysis is completed, the connecting tube 12 is disattached from the catheter 4 as shown in FIG. 4. In accordance with the prior art, the catheter 4 is removed as shown in FIG. 5 and a Deane's prosthesis 14 is introduced into the sinus tract 10 as shown in FIGS. 6 and 7. The sinus tract 10 rests against the flexible pin portion of the Deane's prosthesis 14, in an abutting relationship, with the flanging means of the Deane's prosthesis 14 resting on the epidermis 6 as shown in FIG. 7.

However, prior to the introduction of the Deane's prosthesis 14 into the formed sinus tract 10, or subsequent to the removal of the Deane's prosthesis 14, the sinus tract 10 can be lost making the introduction of a new catheter 4 into the sinus tract 10 impossible without the subsequent use of a trocar stylet 2 with catheter 4. The reformation of a sinus tract 10 allowing the introduction of a new catheter 4 for subsequent dialysis procedures always requires the attendance of a skilled physician and can be associated with morbidity such as bowel bladder, or vascular perforation and/or peritonitis associated with this blind procedure.

Referring to FIGS. 8 through 12 to describe the present invention, FIG. 8 is identical to FIG. 3 with the addition of the hollow outer tubular member 16 of the present invention about to be "sleeved" over the catheter 4 such that said outer tubular member 16 encloses or surrounds the catheter 4. As shown in FIG. 9, the outer tubular member is then gently introduced as surrounding the catheter 4 and through the opening in the epidermis 6 along the sinus tract 10 and may extend just into the peritoneal cavity 8 such that the sinus tract 10 rests against the outer wall of the outer tubular member 16 in an abutting relationship with the catheter 4 resting against the inner wall of the outer tubular member in an abutting relationship.

The above described introduction of the outer tubular member 16 can take place at any time, either before or subsequent to the dialysis procedure. However, it is usually introduced after the catheter 4 is in place within the sinus tract 10 as shown in FIGS. 8 and 9. Prior to its introduction, the outer tubular member 16 can be trimmed in length and shaped to account for variations in sinus tract 10 angle and length which can vary from patient to patient.

After the medical procedure requiring catheterization is completed, such as in for example, the above described peritoneal dialysis procedure, the catheter 4 may be removed from within the outer tubular member 16 while said outer tubular member 16 is kept in place along the sinus tract 10 with the flange 11 resting on the epidermis 6, as shown in FIG. 10, resulting in a continual maintenance of the integrity of the sinus tract 10 as shown in FIG. 10, such never having been available in the prior art.

Thereafter, the sinus tract 10 can be "sealed" with use of the inner cylindrical member 20 shown in FIG. 11. FIG. 11 is identical to FIG. 10 with the addition of a view of the inner cylindrical member 20 about to be introduced into the outer tubular member 16 to effectuate such "sealing" of the sinus tract 10. As shown in FIG. 12, while the outer tubular member 16 is in place along the sinus tract 10, the inner cylindrical member 20 is introduced into the outer tubular member 16 such that said inner tubular member 20 rests along the inner wall of the outer tubular member 16. The inner cylindrical member 20 remains securely in place along the inner wall of the outer tubular member 16 with the cap of said inner cylindrical member 21 resting against the flange 11 of the outer tubular member 16, resulting in the integrity of the sinus tract 10 being maintained and "sealed" to prevent the undesirable introduction of foreign material or bacteria or the undesirable exudation of body fluids.

Referring to FIGS. 10, 11, 12 & 13 when a subsequent catheterization procedure is desired, the inner cylindrical member 20 is removed from the outer tubular member 16, while said outer tubular member is kept in place in the sinus tract 10 resulting in the view shown in FIG. 10. Thereafter, as shown in FIG. 9, a new catheter 4 is introduced into the outer tubular member 16 and said catheter 4 can therefore be easily introduced along the original sinus tract 10 and within the outer tubular member 16, resulting in the catheter 4 being aligned along the sinus tract 10. The introduction of such new catheter 4 into said outer tubular member 16 along said sinus tract 10 may be performed without the attendance of a skilled physician. Since it is no longer a blind procedure with risk of morbidity. Thereafter, a subsequent dialysis can be effectuated and the above procedure repeated to facilitate yet subsequent catheterization procedures. The above results in the continual maintenace of the sinus tract 10 for continual catheterizations. However, it is recommended that periodically (after no more than one week or 5 or 6 catheterization proceedures) that the outer tubular member 16 be replaced with a new sterile outer tubular member 16 in the following manner:

The catheter 4 is held carefully in place and the outer tubular member 16 is removed and discarded. A new sterile outer tubular member 16 is sleeved over the in place catheter 4 in the same manner as shown in FIGS. 8 and 9. When the new catheter 4 is removed the sinus tract 10 is again maintained by the new outer tubular member 16 and is sealed by introduction of a new sterile inner cylindrical member 21 in the same manner as shown in FIGS. 10, 11 and 12.

FIG. 13 is identical to FIG. 12 with the addition of a securing means provided by at least one ridge 22 on the surface of the inner cylindrical member 20 and a complementary groove 24 provided on the inner wall of the outer tubular member 16 such that the inner cylindrical member 20 fits snugly in place within the outer tubular member 16 to prevent inadvertent removal of the inner cylindrical member 20 from the outer tubular member 16.

The above described invention may be comprised of any suitable material, such as plastic or silicone rubber or combination of same, or any other suitable material such that the resultant device is suitably flexible and sterilized or sterilizable for the above described use.

Although the procedure described above relates to use of the invention in connection with the catheterization procedure for the purposes of chronic peritoneal dialysis, the principles of the invention are suitable for the maintenance of the integrity of any epidermal sinus tract formed for the purposes of other medical procedures requiring chronic catheter introduction, such as chronic intermittent laproscopy or chronic catheterization procedures.

Having thus described my invention, what I claim and desire to secure by Letters Patent is:

1. A prosthetic device for maintaining the integrity of a sinus tract formed by a catheter during an initial catheterization for the purposes of medical procedures to enable said tract to be repeatedly used for subsequent catheterization comprising,
   (a) an outer hollow tubular member of uniform diameter and uniform wall thickness for the entire extent thereof adapted to be guided by said catheter into said initially formed sinus tract in surrounding relation with the catheter in the tract formed during said initial catheterization, with flanging means at the external end of said outer hollow tubular member to rest on the epidermis at the beginning of said sinus tract,
   (b) an inner solid cylindrical member adapted to be inserted into said outer hollow tubular member for sealing said sinus tract after said catheter has been withdrawn from said sinus tract following said medical procedure requiring catheterization,
   (c) whereby subsequent removal of said inner solid cylindrical member enables insertion of a new sterile catheter into said outer hollow tubular member along the same initially formed sinus tract to permit another catheterization medical procedure through said tract, and whereby said outer hollow tubular member may easily be replaced while the catheter remains in the tract.

2. A prosthetic device as claimed in claim 1 wherein the outer hollow tubular member and inner solid cylindrical member contain a securing means to prevent inadvertent removal of said inner solid cylindrical member.

3. A prosthetic device as claimed in claim 1 wherein said inner solid cylindrical member fits snugly into said outer hollow tubular member to prevent inadvertent removal of said inner solid cylindrical member.

4. A prosthetic device as claimed in claim 1 wherein said device is comprised of a flexible material.

5. A prosthetic device as claimed in claim 1 wherein said device is comprised of a plastic material.

6. A prosthetic device as claimed in claim 1 wherein said device is comprised of a silicone rubber material.

7. A prosthetic device as claimed in claim 1 wherein said device is comprised of a combination of silicone, rubber and plastic materials.

8. A prosthetic device as claimed in claim 1 wherein said device is comprised of a material which can be subjected to sterilization.

9. A prosthetic device as claimed in claim 2 wherein the securing means is provided by at least one ridge on the inner solid cylindrical member and one corresponding groove in the outer hollow tubular member such that when the inner solid cylindrical member is fitted into the outer hollow tubular member said inner solid cylindrical member fits snugly in place in said outer hollow tubular member.

10. A method of maintaining the integrity of a sinus tract formed in a somatic wall, membrane or tissue structure during an initial catheterization to enable the repeated use of said tract for subsequent catheterization comprising the steps of, (a) inserting a catheter and stylet through said somatic wall, membrane or tissue structure to form a tract therethrough, (b) removing said stylet thereby leaving said catheter in said tract, (c) connecting said catheter to connecting means to enable a medical procedure requiring catheterization to be performed, (d) disconnecting said connecting means upon completion of such medical procedure, (e) guiding an outer hollow tubular member of uniform diameter and uniform wall thickness for the entire extent thereof with flanging means at the external end of said outer hollow tubular member to rest on the epidermis at the beginning of said sinus tract, into said tract in surrounding relation with said catheter, (f) removing said catheter from said tract leaving said outer hollow tubular member in said tract, (g) inserting an inner solid cylindrical member in said outer hollow tubular member for sealing said tract after said catheter has been removed, whereby subsequent removal of said inner solid cylindrical member enables insertion of a new catheter into said outer hollow tubular member through said tract to permit another medical procedure requiring catheterization therethrough.

11. A method in accordance with claim 10 wherein the outer hollow tubular member is withdrawn from the sinus tract and a new outer hollow tubular member is guided therein in surrounding relation with said catheter.

* * * * *